United States Patent
Kim et al.

(10) Patent No.: US 10,500,146 B2
(45) Date of Patent: Dec. 10, 2019

(54) COMPOSITION FOR SKIN WHITENING COMPRISING AMORPHIGENI AS EFFECTIVE INGREDIENT

(71) Applicant: INDUSTRY-ACADEMIC COOPERATION FOUNDATION GYEONGSANG NATIONAL UNIVERSITY, Gyeongsangnam-do (KR)

(72) Inventors: Kwang Dong Kim, Gyeongsangnam-do (KR); Ji Yun Yoo, Gyeongsangnam-do (KR); Soojong Park, Chungcheongnam-do (KR); Sangseok Oh, Gyeongsangnam-do (KR); Dae Wook Kim, Gyeongsangnam-do (KR); Ki Hun Park, Gyeongsangnam-do (KR); Kiwon Lee, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

(*) Notice: Subject to any disclaimer, the term of this patent is extended or adjusted under 35 U.S.C. 154(b) by 0 days.

(21) Appl. No.: 15/768,609

(22) PCT Filed: Oct. 13, 2016

(86) PCT No.: PCT/KR2016/011464
§ 371 (c)(1),
(2) Date: Apr. 16, 2018

(87) PCT Pub. No.: WO2017/065505
PCT Pub. Date: Apr. 20, 2017

(65) Prior Publication Data
US 2018/0303734 A1    Oct. 25, 2018

(30) Foreign Application Priority Data
Oct. 16, 2015 (KR) .................. 10-2015-0144455

(51) Int. Cl.
*A61K 8/49*  (2006.01)
*A61Q 19/02*  (2006.01)
(Continued)

(52) U.S. Cl.
CPC .............. *A61K 8/498* (2013.01); *A23L 33/10* (2016.08); *A61K 8/9789* (2017.08);
(Continued)

(58) Field of Classification Search
None
See application file for complete search history.

(56) References Cited

U.S. PATENT DOCUMENTS 4,696,813 A * 9/1987 Higa .................... A61K 8/4946
424/583

FOREIGN PATENT DOCUMENTS

JP    H6-016531    1/1994
JP    2007-186439 A    7/2007
(Continued)

OTHER PUBLICATIONS

International Search Report for PCT/KR2016/011464.
(Continued)

*Primary Examiner* — Nicole P Babson
(74) *Attorney, Agent, or Firm* — The PL Law Group, PLLC (57) ABSTRACT

A skin whitening composition includes amorphigeni or a salt thereof as an effective ingredient. Amorphigeni suppresses the expression of tyrosinase and induces autophagy on melanosomes. As such, it was confirmed that amorphigeni not only suppresses melanin production but also exhibits the effect of removing melanin previously produced by α-MSH (melanocyte-stimulating hormone). Accordingly, amorphigeni can be advantageously used as a functional material for skin whitening and skin lightening.

20 Claims, 8 Drawing Sheets
Specification includes a Sequence Listing.

(51) Int. Cl.
A61K 31/352 (2006.01)
A23L 33/10 (2016.01)
A61K 8/9789 (2017.01)
(52) U.S. Cl.
CPC .......... *A61K 31/352* (2013.01); *A61Q 19/02* (2013.01); *A23V 2002/00* (2013.01); *A23V 2200/318* (2013.01)

(56) References Cited

FOREIGN PATENT DOCUMENTS

| JP | 2007-186441 A | 7/2007 |
|---|---|---|
| JP | 2007-186442 A | 7/2007 |
| KR | 10-2015-0029305 A | 3/2015 |
| KR | 10-2015-0050995 A | 5/2015 |
| KR | 10-1525090 B1 | 6/2015 |
| KR | 10-1551106 B1 | 9/2015 |

OTHER PUBLICATIONS

Young Soo Kim et al., "Flavanones and rotenoids from the roots of *Amorpha fruticosa* L. that inhibit bacterial neuraminidase", Food and Chemical Toxicology, vol. 49, No. 8, pp. 1849-1856, 2011.

Kenji Ohguchi et al., "Effects of Sesquiterpene Lactones on Melanogenesis in Mouse B16 Melanoma Cells", Biological & pharmaceutical bulletin, vol. 32(2), pp. 308-310, 2009.

Jeong-yeh Yang et al., "Stimulation of melanogenesis by scoparone in B16 melanoma cells", Acta Pharmacologica Sinica, vol. 27 (11), pp. 1467-1473, 2006.

Office action dated Feb. 5, 2019 from Japan Intellectual Property Office in a counterpart Japanese Patent Application No. 2018-518632 (English translation is also submitted herewith.).

European Search Report for EP16855722.1 dated Mar. 11, 2019 from European patent office in a counterpart European patent application.

Leslie Crombie et al., "Review article No. 135 Biosynthesis in the Rotenoid group of Natural Products: Applications of Isotope Methodology", Phytochemistry, vol. 49, No. 6, pp. 1479-1507, 1998.

Hiroki Terada et al., "A Novel Rotenoids from Amorpha Fruticosa", Proceedings of Natural Organic Compound Symposium, pp. 502-509, 1992 DOI: https://www.jstage.jst.go.jp/article/tennenyuki/34/0/34_502/_article/-char/ja/ (English abstract is submitted herewith.).

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
ggccagcttt caggcagagg t                                                   21
```

```
<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tggtgcttca tgggcaaaat c                                              21
```

COMPOSITION FOR SKIN WHITENING COMPRISING AMORPHIGENI AS EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/011464, filed Oct. 13, 2016, which claims priority to the benefit of Korean Patent Application No. 10-2015-0144455 filed in the Korean Intellectual Property Office on Oct. 16, 2015, the entire contents of which are incorporated herein by reference.

TECHNICAL FIELD

The present invention relates to a composition for skin whitening comprising amorphigeni as an effective ingredient. More specifically, the present invention relates to a composition having a skin whitening function containing amorphigeni, which is derived from *Amorpha fruticosa*, characterized by inhibition of melanin production and reduction of previously formed melanin through suppressing the activities of tyrosinase.

BACKGROUND ART

Among the tissues of a human body, skin is directly exposed to an external environment and plays a role of a protective wall between the inside of a human body and an external environment. It provides a protection against external environment-contaminating substances including chemical substances, ultraviolet rays and invasion by microorganisms, and thus protects a living body from a surrounding environment. Skin color is determined by melanin, hemoglobin, carotene, or the like, and melanin plays the most important role among them. In addition to the determination of human skin color, melanin performs a skin protection function like ultraviolet absorption activity, activity of a free radical scavenger, or the like. However, when excessive production of melanin is caused by a change in external environment like excessive exposure to ultraviolet rays, air pollution, stress, or the like, the pigmentation phenomenon occurs in skin to yield skin melanism, small brown spots, freckles, or the like. Skin melanism is caused by the reaction of skin cells against internal and external factors, and the most representative cause is exposure to ultraviolet rays. Namely, once a skin is exposed to ultraviolet rays, tyrosinase is activated. As the tyrosinase activates tyrosine present in skin tissue to oxidize DOPA (dihydroxyphenylalanine) and dopaquinone to produce melanin in the melanocyte of skin pigment cell, melanocyte. This melanin is transferred to keratinocyte of skin and protects skin from ultraviolet rays by keratinization process. As such, melanin is an ultraviolet protecting agent that is essentially required in human body, and it also plays a role of an effective free radical scavenger for removing various radicals that can cause deformation of biological components like protein, lipid, and nucleic acid. However, if there is locally excessive production of melanin or deterioration of a physiological function of skin which is diminished by aging or skin lesion, melanin is precipitated on a skin surface to yield small brown spots, freckles, and various pigmentations. Since the cause and mechanism of skin melanism are known as described in the above, for producing a skin whitening cosmetics, a method of blending materials having an inhibitory effect on the activity of tyrosinase, which is an enzyme involved with a skin melanism process, or a method of reducing melanin production by inhibiting part of the reactions during melanin production process is generally used. Representative materials used for such purpose include chemical materials such as ascorbic acid, kojic acid, or hydroquinone, and plant extracts such as mulberry root skin extract or liquorice extract. However, ascorbic acid is not suitable as a melanin production inhibitor because it has not only an insufficient inhibitory effect on tyrosinase activity but also poor stability of the molecule itself. Although kojic acid is excellent in inhibitory activity on tyrosinase, there is a problem in terms of the stability like discoloration after blending in cosmetic materials and lower potency according to a change over time, and, due to significant skin irritation, it has a limitation in terms of actual use. Use of hydroquinone as a cosmetic material is also limited due to a problem related to skin irritation and safety. Therefore, there is growing interest in development of a novel and effective skin whitening component.

Meanwhile, in Japanese Patent Application Laid-Open No. 1994-016531, a cosmetic material is disclosed, and in Korean Patent Registration No. 1525090, a cosmetic composition for skin whitening is disclosed. However, there is no disclosure relating to a composition for skin whitening comprising, as an effective ingredient, amorphigeni of the present invention.

SUMMARY

The present invention is devised in view of the demand described above, and the inventors of the present invention isolated and extracted amorphigeni from roots of *Amorpha fruticosa*, and confirmed that amorphigeni of the present invention not only suppresses melanin production but also exhibits the effect of removing previously formed melanin through the suppression of tyrosinase and the induction of autophagy on melanosomes. The present invention is completed accordingly.

In order to achieve the object described above, the present invention provides a cosmetic composition for skin whitening comprising amorphigeni or a cosmetically acceptable salt thereof as an effective ingredient.

The present invention further provides a pharmaceutical composition for preventing or treating a melanin hyperpigmentation disorder comprising amorphigeni or a pharmaceutically acceptable salt thereof as an effective ingredient.

The present invention still further provides a functional health food composition for preventing or improving a melanin hyperpigmentation disorder comprising amorphigeni or a pharmaceutically acceptable salt thereof as an effective ingredient.

The present invention relates to a composition for skin whitening comprising amorphigeni as an effective ingredient. Amorphigeni of the present invention suppresses the expression of tyrosinase and induces autophagy on melanosomes. Thus, it was confirmed that amorphigeni of the present invention not only suppresses melanin production but also exhibits the effect of removing melanin previously produced by α-MSH (melanocyte-stimulating hormone). As such, amorphigeni of the present invention can be advantageously used as a functional material for skin whitening and skin lightening.

DETAILED DESCRIPTION

To achieve the object of the present invention, the present invention provides a cosmetic composition for skin whitening comprising amorphigeni represented by the following chemical formula 1 or a cosmetically acceptable salt thereof as an effective ingredient.

[Chemical formula 1]

The effective ingredient of the cosmetic composition for skin whitening according to the present invention is amorphigeni which has a structure represented by the above chemical formula 1. Amorphigeni of the present invention reduces melanin production in melanin cells and previously accumulated melanin in significant sense, and thus has an activity of skin whitening.

As for the cosmetically acceptable salt which can be used as an effective ingredient of the composition of the present invention, an acid addition salt formed with a cosmetically acceptable free acid is useful. The acid addition salt can be produced by a common method, e.g., a compound is dissolved in an excessive amount of an aqueous acid solution and the resulting salt is precipitated by using a water-miscible organic solvent such as methanol, ethanol, acetone, or acetonitrile. It is also possible that the compound and acid or alcohol (e.g., glycol monomethyl ether) in water, both in an equimolar amount, are heated and subsequently the mixture is dried by evaporation, or precipitated salts are filtered by suction. In that case, an organic acid or an inorganic acid can be used as a free acid. As for the inorganic acid, hydrochloric acid, phosphoric acid, sulfuric acid, nitric acid, stannic acid, or the like can be used, and as for the organic acid, methane sulfonic acid, p-toluene sulfonic acid, acetic acid, trifluoroacetic acid, maleic acid, succinic acid, oxalic acid, benzoic acid, tartaric acid, fumaric acid, mandellic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid, or the like can be used, but the inorganic acid and organic ac id are not limited to them.

Meanwhile, the skin whitening effect intends to mean an effect of improving or preventing darkish skin, small brown spots, freckles, or dark circles which occur due to various causes including exposure to ultraviolet rays, a change in hormone balance, or a genetic program, an effect of obtaining a beautiful skin with translucent feel or maintaining a beautiful skin with translucent feel, or an effect of enhancing shine and tight feeling by reducing the darkish feeling of a skin. In general, a darkish skin, small brown spots, freckles, or dark circles are known to occur due to the precipitation of biosynthesized melanin pigment on skin as melanocytes are stimulated by ultraviolet rays or a change in hormone balance. Accordingly, if melanin production is suppressed, it becomes possible to prevent or improve a darkish skin, small brown spots, freckles, or dark circles.

The function of amorphigeni to suppress melanin production was determined by a test method in which cultured pigment cells are used. The pigment cells indicate cells which have a function of producing melanin, and when they are cultured in general, melanin pigment is precipitated to yield dark pigmentation. On the other hand, if a material having a function of suppressing melanin production is present in the culture system, the melanin production is suppressed to yield relative whitening. Based on the degree of this relative whitening, the function of suppressing melanin production can be predicted.

According to the cosmetic composition for skin whitening of the present invention, amorphigeni may be amorphigeni which has been isolated from roots of *Amorpha fruticosa*, but it is not limited thereto.

According to the cosmetic composition for skin whitening of the present invention, the amorphigeni may inhibit the activity of tyrosinase, but it is not limited thereto.

According to the cosmetic composition for skin whitening of the present invention, the amorphigeni may suppress production of melanin or remove previously formed melanin, but it is not limited thereto.

According to the cosmetic composition for skin whitening of the present invention, the cosmetic composition for skin whitening can have any one formulation selected from a group consisting of an ointment for external skin application, a crème, a softening cosmetic water, a nutritional cosmetic water, a pack, an essence, a hair toner, a shampoo, a rinse, a hair conditioner, a hair treatment, a gel, a skin lotion, a skin softener, a skin toner, an astringent, a lotion, a milk lotion, a moisture lotion, a nutritional lotion, a massage crème, a nutritional crème, a moisture crème, a hand crème, a foundation, a nutritional essence, a sunscreen, a soap, a cleansing foam, a cleansing lotion, a cleansing crème, a body lotion, and a body cleanser, but it is not limited thereto. The cosmetic composition constituting each of those formulations may contain various bases and additives that are necessary and suitable for preparing those formulations, and the type and amount of the components can be easily selected by a person skilled in the pertinent art.

The cosmetic composition of the present invention may further contain, other than the effective ingredient, one or more kinds of a skin whitening active component which exhibits the same or similar activity. Examples of the skin whitening active component include kojic acid and derivatives thereof, albutin, ascorbic acid and derivatives thereof, hydroquinone and derivatives thereof, resorcinol, cycloalkanone, methylene dioxyphenylalkanol, 2,7-dinitroindazole, and plant extracts such as bearberry extract, rice extract, or liquorice extract, but it is not limited thereto.

In a case in which the cosmetic composition of the present invention has a formulation of paste, crème, or gel, animal fibers, plant fibers, wax, paraffin, starch, tragacanth, cellulose derivatives, polyethylene glycol, silicone, bentonite, silica, talc, or zinc oxide can be used as a carrier component.

In a case in which the cosmetic composition of the present invention has a formulation of powder or spray, lactose, talc, silica, aluminum hydroxide, calcium silicate, or polyamide powder can be used as a carrier component. In a case in which the cosmetic composition is a spray, in particular, a propellant such as chlorofluorohydrocarbon, propane-butane, or dimethyl ether can be additionally included.

In a case in which the cosmetic composition of the present invention has a formulation of solution or emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propyplene glycol, 1,3-butylglycol oil, glycerol aliphatic ester, polyethylene glycol, and fatty acid ester of sorbitan.

In a case in which the cosmetic composition of the present invention has a formulation of suspension, a liquid phase diluent such as water, ethanol or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

In a case in which the cosmetic composition of the present invention has a formulation of surfactant-containing cleanser, aliphatic alcohol sulfate, aliphatic alcohol ether sulfate, sulfonsuccinic acid monoester, acethionate, imidazoilum derivatives, methyl taurate, sarcosinate, fatty acid amide ether sulfate, alkylamidobetain, aliphatic alcohol, fatty acid glyceride, fatty acid diethanolamide, plant oil, linolin derivatives, or ethoxylated glycerol fatty acid ester can be used.

The cosmetic composition of the present invention may additionally contain a vehicle including a fluorescent material, a bactericidal agent, a hydrotrope, a moisturizing agent, an aroma, an aromatic carrier, a protein, a solubilizing agent, sugar derivatives, a sunshine blocking agent, a vitamin, a plant extract, or the like.

The present invention further provides a pharmaceutical composition for preventing or treating a melanin hyperpigmentation disorder comprising amorphigeni or a pharmaceutically acceptable salt thereof as an effective ingredient.

The salt is not particularly limited as long as it is pharmaceutically acceptable, and hydrochloric acid, sulfuric acid, nitric acid, phosphoric acid, hydrogen fluoride acid, hydrogen bromide acid, formic acid, acetic acid, tartaric acid, lactic acid, citric acid, fumaric acid, maleic acid, succinic acid, methane sulfonic acid, benzene sulfonic acid, toluene sulfonic acid, naphthalene sulfonic acid, or the like can be used, for example. Other than the acid addition salt, a base addition salt such as sodium hydroxide, potassium hydroxide, triethylamine, or tertiary butylamine can be also used.

The term "melanin hyperpigmentation" used in this specification means blackening or darkening of a certain area of a skin, a finger nail, or a toe nail as caused by excessively increased melanin when compared to other area. Examples of the melanin hyperpigmentation include freckles, senile spots, chloasma, small brown spots, brown or black moles, sunshine pigment spots, cyanic melisma, hyperpigmentation after drug use, gravidic chloasma, hyperpigmentation after inflammation caused by lesions or skin inflammation like excoriation and burn, but it is not limited thereto.

The pharmaceutical composition of the present invention may contain a pharmaceutically acceptable carrier in addition to the effective ingredient. The carrier is a material which is commonly used for producing a preparation, and examples thereof include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil, but it is not limited thereto. The pharmaceutical composition of the present invention may additionally contain, other than those components, a lubricating agent, a humidifying agent, a sweetening agent, a flavoring agent, an emulsifying agent, a suspending agent, a preservative, or the like. Suitable pharmaceutically acceptable carriers and preparations are described in detail in Remington's Pharmaceutical Sciences, 19th ed., 1995.

Preferable dosage of the pharmaceutical composition of the present invention may vary depending on various factors like a method for preparation, administration mode, age, weight, and state of a patient, food, administration period, administration route, excretion rate, and response sensitivity. Meanwhile, the dosage of the pharmaceutical composition of the present invention is preferably 0.0001 to 100 mg/kg of bodyweight per day.

The pharmaceutical composition of the present invention can be administered either orally or parenterally, and in case of parenteral administration, the administration can be made by topical application on skin, intravenous injection, subcutaneous injection, intramuscular injection, peritoneal injection, or transdermal administration. Considering that the pharmaceutical composition of the present invention is used for a treatment or a prevention of a melanin hyperpigmentation disorder, the administration is preferably achieved by topical application of the composition on skin.

Concentration of the effective ingredient which is included in the composition of the present invention can be determined in consideration of treatment purpose, state of a patient, required period, or the like, and it is not limited to the concentration of a specific range.

The pharmaceutical composition of the present invention can be produced in unit dose form or by adding it to a multi-dose container according to formulation using a pharmaceutically acceptable carrier or vehicle by following a method that can be easily carried out by a person who has common knowledge in the field to which the present invention pertains. In that case, the formulation can be any one formulation selected from an injection solution, a crème, a patch, a spray, an ointment, a hard solid, a lotion, a liniment, a pasta, and a cataplasma, and a dispersing agent or a stabilizing agent may be additionally contained therein.

The present invention still further provides a functional health food composition for preventing or improving a melanin hyperpigmentation disorder comprising amorphigeni or a pharmaceutically acceptable salt thereof as an effective ingredient.

In a case in which the functional health food composition of the present invention is used as a food additive, the functional health food composition can be added directly or used with other food or other components, and it can be suitably used according to a common method. The mixing amount of the effective ingredient can be suitably used according to the purpose of use (i.e., prevention or amelioration). In general, for producing a food product or a drink, the functional health food composition of the present invention is added in an amount of 15 part by weight or less, and preferably 10 parts by weight or less relative to the raw materials. However, in case of application for a long period of time like achieving health and hygiene, or having health management, the amount may be lower than the aforementioned range as there is no problem in terms of the safety, and thus the effective ingredient may be also used in an amount that is higher than the aforementioned range.

Type of the functional health food is not particularly limited. Examples of the food to which the functional health food composition can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all health foods in general sense are included therein.

The functional health food composition of the present invention can be also prepared as a food, in particular, a functional food. The functional food according to the present invention contains the components that are generally added for preparing a food, and examples thereof include proteins, carbohydrate, fats, nutrients, and flavoring agents. When it is prepared as a drink, for example, natural carbohydrates or a flavoring agent may be included as an additional component other than the effective ingredient. The natural carbohydrates are preferably monosaccharides (for example, glucose, fructose, and the like), disaccharides (for example, maltose, sucrose, and the like), oligosaccharides, polysaccharides (for example, dextrin, cyclodextrin, and the like), or sugar alcohols (for example, xylitol, sorbitol, erythritol, and the like). As for the flavoring agent, a natural flavoring agent (for example, thaumatin, stevia extract, and the like) and a synthetic flavoring agent (for example, saccharine, aspartame, and the like) can be used.

Other than those described above, the functional health food composition may further contain various kinds of a nutritional agent, vitamins, an electrolyte, flavors, a coloring agent, pectinic acid and salts thereof, alginic acid and salts thereof, organic acids, a protective colloid thickening agent, a pH adjusting agent, a stabilizing agent, a preservative, glycerin, alcohol, and a carbonating agent used for carbonate drink. Although the ratio of those components to be added is not critically important, it is generally selected from a range of from 0.01 to 0.1 part by weight relative to 100 parts by weight of the functional health food composition of the present invention.

Hereinbelow, the present invention is explained in greater detail in view of the Examples. However, it is evident that the following Examples are given only for specific explanation of the present invention and it would be obvious to a person who has common knowledge in the pertinent art that by no means the present invention is limited to the following Examples.

Materials and Methods

1. Isolation and Extraction of Amorphigeni

In order to isolate and extract amorphigeni, 5 liter of acetone was added to 0.5 kg of roots of *A. fruticosa*, which have been prepared by drying in shade, followed by extraction for 7 days. The extract was concentrated under reduced pressure to obtain 21 g of concentrate. The prepared concentrate was then subject to the first isolation by using silica gel column (10×30 cm). At that time, hexane and acetone were used as a solvent for elusion, and by performing elution using a mixture solvent of hexane and acetone while increasing the polarity (i.e., from 100:1 of hexane and acetone to 100% (v/v) acetone), seven fractions (A to G) were obtained. By concentrating fraction C in which amorphigeni as a target compound is contained in a large amount, a concentrate was obtained in an amount of 1.3 g. The obtained concentrate in an amount of 1.3 g was then subjected to silica gel chromatography at conditions of using a mixture solvent of hexane and acetone (4:1). Accordingly, amorphigeni with purity of 70% or higher was obtained in an amount of 160 mg. The obtained fraction was subjected to gel chromatography (Sephadex LH-20) in which elution is made with 80% (v/v) methanol, and thus amorphigeni with purity of 98% was obtained in an amount of 29 mg. Structure of the obtained compound was identified by using $^1$H-NMR, $^{13}$C-NMR, 2D-NMR, DEPT, and mass analyzer.

2. Cell Culture and Compounds

B16F10 mouse melanoma cell line was provided by ATCC (American Type of Culture Collection, USA). The cells were cultured in DME (Dulbecco's Modified Eagle's), which has been added with 10% FBS (fetal bovine serum) and 1% penicillin/streptomycin (Sigma-Aldrich, USA), in a 5% $CO_2$ humidifying incubator at 37 t condition. α-MSH (melanocyte-stimulating hormone) and 3-MA (3-methyladenine) were purchased from Sigma-Aldrich, USA, tyrosine-EDTA was purchased from Lonza, USA, and MTT ([3-(4, 5-dimethylthiazol-2-yl)-2,5-diphenyl tetrazolium bromide) was purchased from Amresco, USA, and they were used for the following Examples.

3. Measurement of Cell Viability

B16F10 cells were cultured for 24 hours in a 96-well plate. Thereafter, they were treated with amorphigeni at various concentrations, and cultured for 24 hours. Subsequently, a MTT solution (5 μg/mL) was added to the cells, which were then cultured for 3 hours. After removing the medium and treating the cells with DMSO, the cells were cultured for 20 minutes. By using a microplate reader (Bio-Rad), absorbance at 595 nm was measured.

4. Measurement of Melanin Content

Measurement of melanin content was carried out by slightly modifying the method by Yang et al. (Yang et al., 2006, Acta pharmacologica Sinica 27, 1467-73). Specifically, B16F10 cells were inoculated into a 6-well plate and cultured for 24 hours. Thereafter, the cells were treated with amorphigeni and α-MSH, each at 1 μM, followed by culture for 48 hours. The cultured cells were collected after being subjected to trypsinization and dissolution in 1 N NaOH containing DMSO for 24 hours at 65° C. By using a microplate reader (Bio-Rad), melanin content was measured at 415 nm.

5. Measurement of Tyrosinase Activity

Tyrosinase activity was measured by slightly modifying the method by Ohgushi et al. (Ohgushi et al., 2009, Biological & Pharmaceutical Bulletin 32, 308-10). Specifically, B16F10 cells were inoculated into a 6-well plate and cultured for 24 hours. Thereafter, the cells were treated with amorphigeni and α-MSH, each at 1 μM, followed by culture for 48 hours. The cultured cells were collected and dissolved with 1% Triton X-100 solution for 1 hour on ice. The proteins were cultured for 4 hours with 100 μl (2 mg/ml) L-DOPA in a 5% $CO_2$ humidifying incubator at 37° C. condition. After that, by using a microplate reader (Bio-Rad), absorbance at 490 nm was measured.

6. RNA Extraction and RT-PCR

Total RNA was extracted from the cells by using RiboEX reagent (GeneAll Biotechnology Co. Ltd, Seoul, South Korea). cDNA was synthesized by using 2 μg of RNA based on reverse transcription (Thermo Scientific, Waltham, Mass., USA). PCR was carried out by using Solg™ e-Taq DNA polymerase kit (SolGent Co. Ltd, Daejeon, South Korea), and each primer described in the following Table 1 was used for PCR.

TABLE 1

Primers used in the present invention

| Target gene | SEQ ID No. | Forward direction/ Reverse direction | Nucleotide sequence |
|---|---|---|---|
| Tyrosinase | 1 | Forward direction | GGCCAGCTTTCAGGCAGAGGT (SEQ ID NO. 1) |

TABLE 1-continued

Primers used in the present invention

| Target gene | SEQ ID No. | Forward direction/ Reverse direction | Nucleotide sequence |
|---|---|---|---|
| | 2 | Reverse direction | TGGTGCTTCATGGGCAAAATC (SEQ ID NO. 2) |

7. Western Blot Analysis

Total proteins were extracted by using RIPA dissolving buffer (50 mM Tris-HCl (pH 8.0), 150 mM NaCl, 1% NP-40, 0.5% sodium dioxycholate and 0.1% SDS). The proteins were separated on a 10 to 15% SDS-PAGE, and transferred to a PVDF membrane (Millipore, Billerica, Mass., USA). The membrane was then incubated with 5% skim milk and primary antibody for 1 hour in TBS (Tris-buffer saline) containing 0.1% Tween 20. The antibody against tyrosinase was purchased from Santa Cruz Biotechnology, USA. ATG5 was purchased from CST (Cell Signaling Technology, USA). The antibody against PMEL was purchased from Abcam (UK).

8. Gene Silencing siRNA made suitable to mouse ATG5 siRNA was synthesized from Genolution (Seoul, South Korea). B16F10 cells were infected with siATG5 by using Lipofectamine 3000 (Invitrogen, Carlsbad, Calif., USA) according to the manufacturer's instructions. Then, after treating the cells with amorphigeni (10 μM) and α-MSH (1 μM) for 48 hours, the results were determined.

9. Statistical Analysis

All data were analyzed by using unpaired Student's t-test, and the results were considered to be statistically significant in case of having $P<0.05$.

Figure 1:
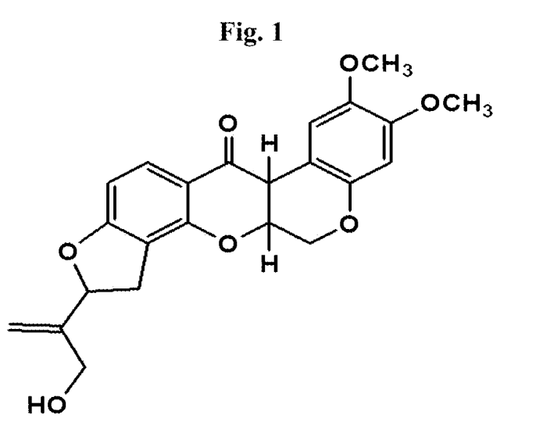
FIG. 1 shows the chemical structure of amorphigeni according to one example of the present invention, which has been isolated and purified from roots of *Amorpha fruticosa*.
Figure 2:
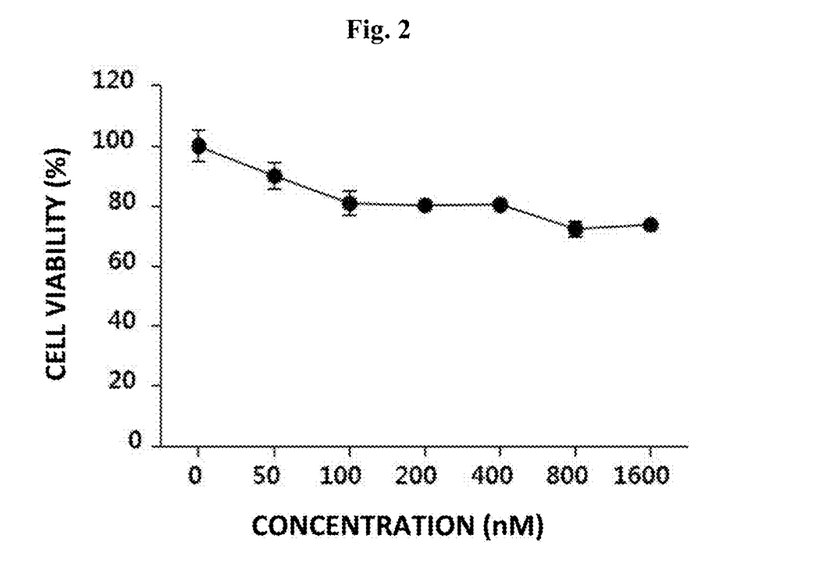
FIG. 2 shows cell viability when B16F10 mouse melanoma cells are treated with amorphigeni at the indicated concentrations according to one example of the present invention.
Figure 3:
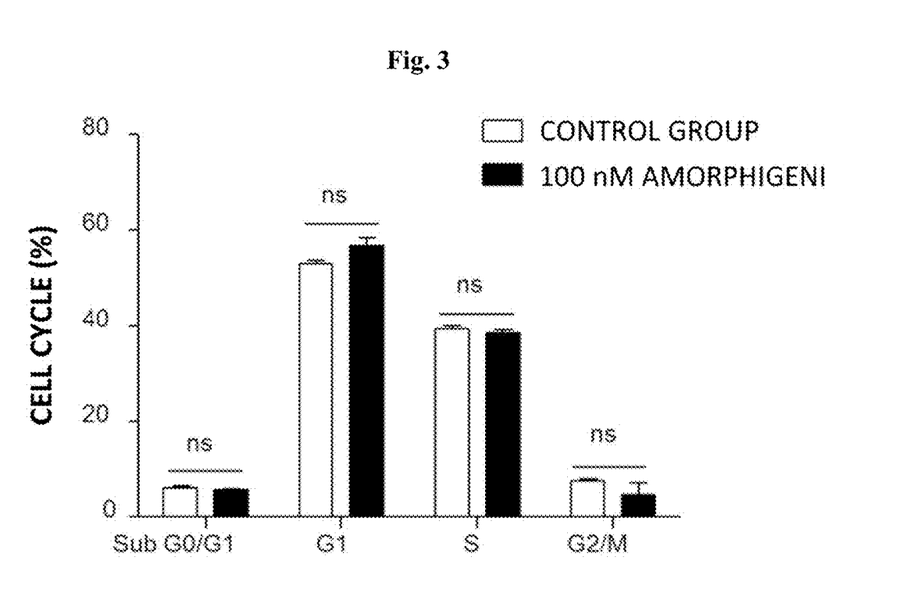
FIG. 3 shows the result of measuring the cell cycle of B16F10 mouse melano cells, in which the melano cells are treated with amorphigeni according to one example of the present invention, stained with PI (propidium iodide), and then subjected to the cell cycle measurement by using a flow cytometer.

Example 1. Analysis of Cell Viability According to Treatment with Amorphigeni of the Present Invention In Example 1, to find out functional plant metabolites which induce depigmentation in melanin cells, amorphigeni was isolated from roots of *Amorpha fruticosa* (FIG. 1). To determine the cytotoxicity of amorphigeni, B16F10 cells were treated with amorphigeni at various concentrations followed by culture for 24 hours. Then, based on MTT (3-(4,5-dimethylthiazol-2-yl)-2,5-diphenyltetrazolium bromide) analysis, cell viability was determined. As a result, it was found as shown in FIG. 2 that, low cytotoxicity is exhibited by amorphigeni at 100 nM and 1600 nM but without inducing any cell death (FIG. 3).

Figure 4A:
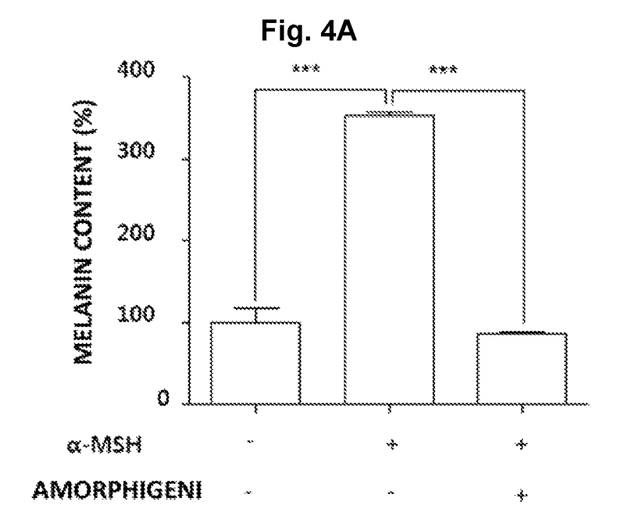
FIGS. 4A and 4B show the effect of lowering melanin content (FIG. 4A) and L-DOPA oxidation (FIG. 4B) in B16F10 mouse melanoma cells after a treatment with α-MSH and amorphigeni according to one example of the present invention.
Figure 4B:
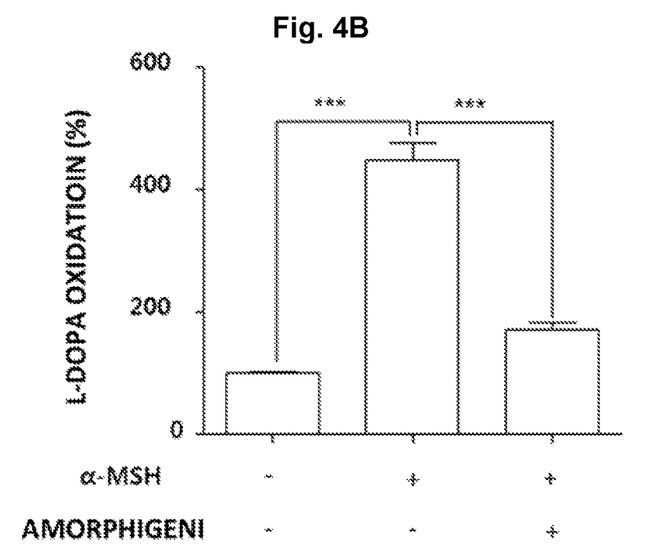

Example 2. Effect of Lowering Melanin Content According to Treatment with Amorphigeni of the Present Invention In order to see whether or not amorphigeni can suppress the pigmentation induced by α-MSH (melanocyte-stimulating hormone), B16F10 cells were treated with α-MSH and amorphigeni, either separately or simultaneously, followed by incubation for 72 hours. As a result, as it is shown in FIGS. 4A and 4B, the melanin content and oxidation level of L-DOPA have significantly increased when the treatment is carried out only with α-MSH, while they tend to decease when the treatment is carried out with both of amorphigeni and α-MSH. Namely, it was able confirm that, by reducing melanin content, amorphigeni of the present invention can suppress depigmentation.

Figure 5:
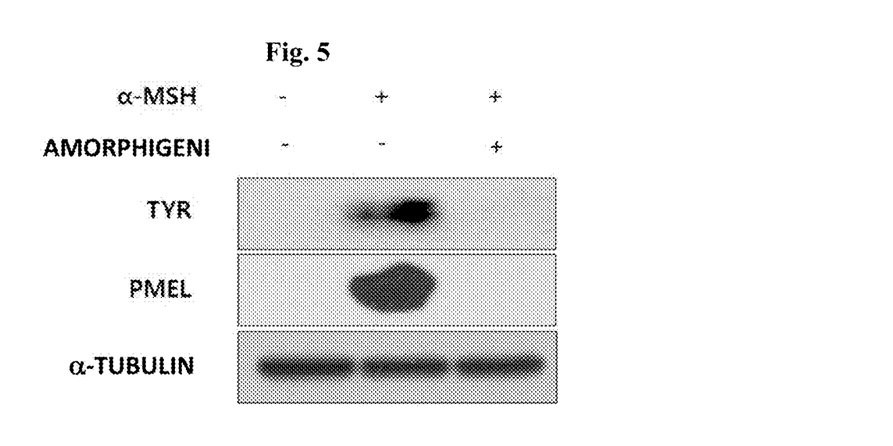
FIG. 5 shows an inhibitory activity on expression of TYR (tyrosinase) and PMEL (premelanosome protein) in B16F10 mouse melanoma cells when they are treated with α-MSH and amorphigeni according to one example of the present invention. α-Tubulin is a loading control.

Example 3. Proteasome-Nondependent Melanosome Removing Effect According to Treatment with Amorphigeni of the Present Invention After treating B16F10 melanin cells with α-MSH alone or both of α-MSH and amorphigeni for 48 hours, protein expression level was measured by Western blot for each of tyrosinase (TYR) and PMEL (premelanosome protein). As a result, as it is shown in FIG. 5, the protein expression amount of tyrosinase and PMEL, which are induced by α-MSH, was effectively lowered by amorphigeni of the present invention.

Figure 6:
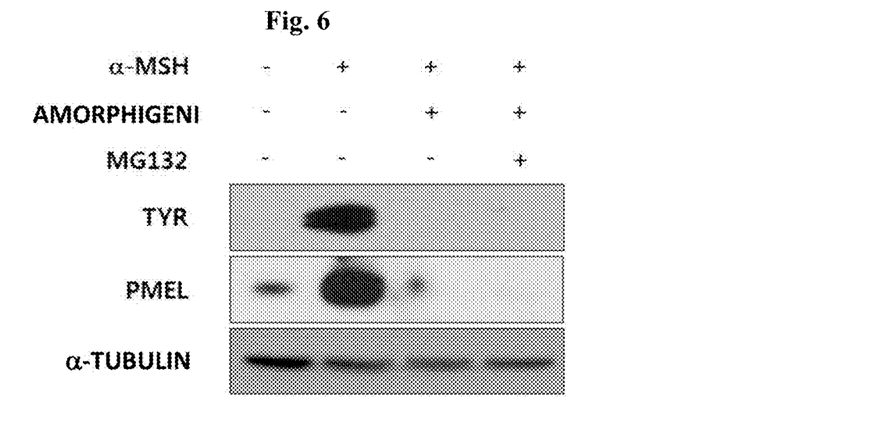
FIG. 6 shows the expression amount of TYR (tyrosinase) and PMEL (premelanosome protein) in B16F10 mouse melanoma cells when they are treated with α-MSH, amorphigeni, and MG132 according to one example of the present invention. α-Tubulin is a loading control; and MG132 is a proteasome inhibitor.

In order to determine whether or not amorphigeni causes degradation of tyrosinase and PMEL protein by inducing a proteasome-dependent proteolytic process, B16F10 melanin cells were treated with α-MSH, amorphigeni, and MG132 as a proteasome inhibitor all together for 48 hours. After that, as a result of measuring the protein expression level of tyrosinase and PMEL based on Western blot, it was shown that the protein expression amount of tyrosinase and PMEL does not increase again in the cells that have been treated with α-MSH, amorphigeni, and MG132 all together, as shown in FIG. 6. Based on those results, it is believed that the depigmentation effect of amorphigeni is not mediated by a proteasome-dependent proteolysis process, but occurs through other different mechanism.

Figure 7:
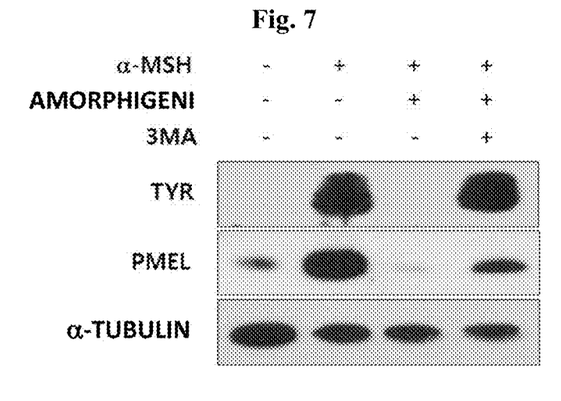
FIG. 7 shows a change in the expression amount of TYR and PMEL (premelanosome protein) in B16F10 mouse melanoma cells when they are treated with α-MSH, amorphigeni, and 3-MA (3-methyladenine) according to one example of the present invention. α-Tubulin is a loading control; and 3-MA is an autophagy inhibitor.

Example 4. Autophagy-Dependent Melanosome Removing Effect According to Treatment with Amorphigeni of the Present Invention In order to confirm whether or not amorphigeni causes degradation of tyrosinase and PMEL proteins by inducing an autophagy process, B16F10 melanin cells were treated with α-MSH, amorphigeni, and 3MA (3-methyladenine) as an autophagy inhibitor all together for 48 hours. After that, the protein expression level of tyrosinase and PMEL was measured based on Western blot. As a result, the cells treated with α-MSH, amorphigeni, and 3MA all together showed the protein expression amount of tyrosinase and PMEL increased again, which has been lowered when the cells were treated with α-MSH and amorphigeni, as shown in FIG. 7.

Figure 8:
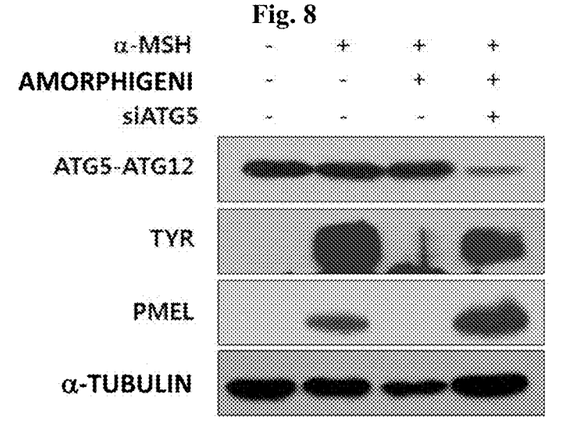
FIG. 8 shows a change in the expression amount of ATG5-ATG12, TYR, and PMEL (premelanosome protein) in B16F10 mouse melanoma cells when they are treated with siATG5 obtained by knockdown of ATG5 (autophagy-related gene 5) followed by treatment with α-MSH and amorphigeni according to one example of the present invention. α-Tubulin is a loading control.

Furthermore, in order to confirm whether or not inhibition of ATG5 (autophagy-related gene 5), which is related with elongation of autophagosomes playing an important role in an autophagy process, can exhibit any effect on amorphigeni-mediated depigmentation, B16F10 melanin cells were transfected with siATG5 (knockdown form of ATG5) for 48 hours to suppress the autophagy. As a result, as it is shown in FIG. 8, when the treatment is carried with both of α-MSH and amorphigeni after suppressing the autophagy by transfection with siATG5, the protein expression amount of tyrosinase and PMEL has increased again while the expression amount of ATG5-ATG12, which binds during the process of forming autophagosomes, has decreased. Namely, it was possible to confirm that amorphigeni can remove melanin by inducing autophagy in B16F10 cells.

Figure 9A:
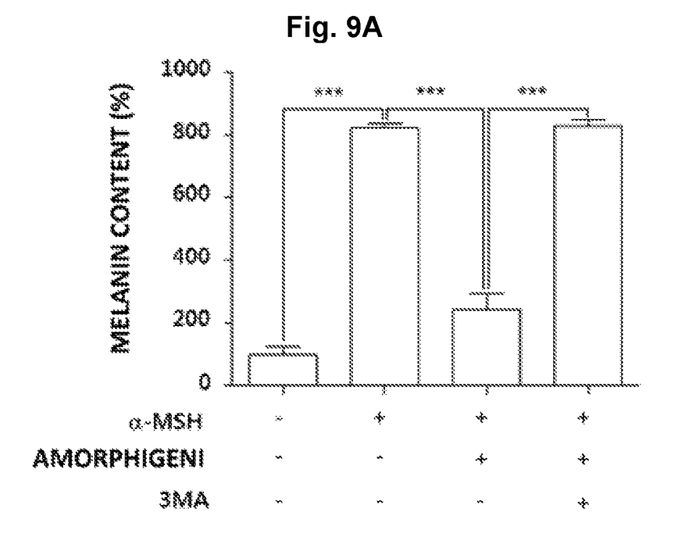
FIGS. 9A and 9B show melanin content (FIG. 9A) and L-DOPA oxidation level (FIG. 9B) in B16F10 mouse melanoma cells when they are treated with α-MSH, amorphigeni, and 3-MA (3-methyladenine) according to one example of the present invention. α-Tubulin is a loading control; and 3-MA is an autophagy inhibitor.
Figure 9B:
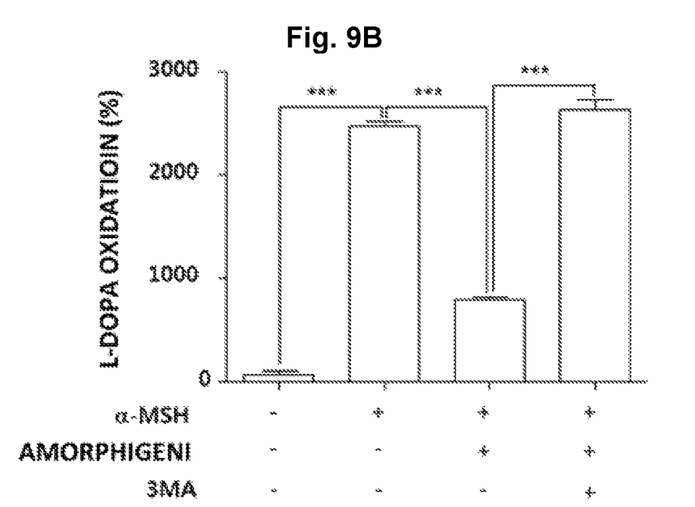

Furthermore, after treating B16F10 melanin cells with α-MSH, amorphigeni, and 3MA all together for 48 hours, the melanin content and oxidation level of L-DOPA were measured (*$P \leq 0.001$). As a result, as shown in FIGS. 9A and 9B**, the cells treated with α-MSH, amorphigeni, and 3MA all together can have the melanin content and oxidation level of L-DOPA that are increased again compared to those lowered by a treatment with α-MSH and amorphigeni.

Figure 10:
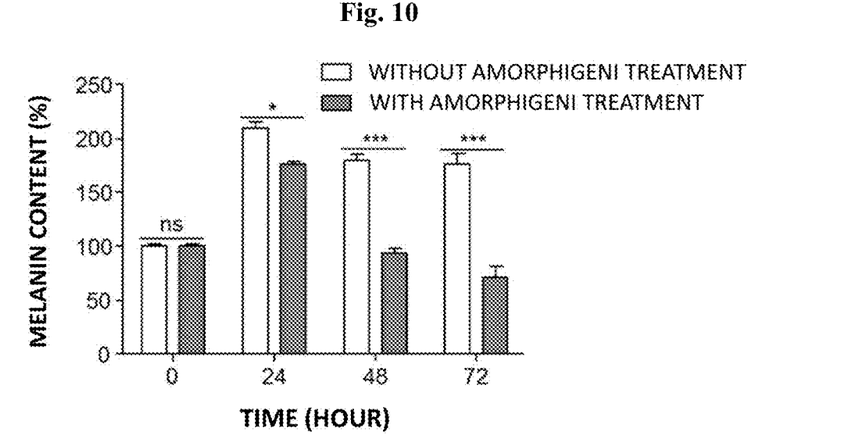
FIG. 10 shows a decrease in the content of previously formed melanin when melanosome synthesis is carried out by a treatment with α-MSH followed by a treatment with amorphigeni according to one example of the present invention.

Example 5. Effect of Degrading Previously Formed Melanosome According to Treatment with Amorphigeni of the Present Invention In order to confirm whether or not amorphigeni causes degradation of melanosomes which have been previously produced by α-MSH, B16F10 melanin cells were treated for 48 hours with α-MSH to have synthesis of melanosomes. Thereafter, the cells were treated with amorphigeni for 48 hours, and melanin content was measured. As a result, the content of the previously formed melanin was effectively lowered as it is shown in FIG. 10.

Figure 11:
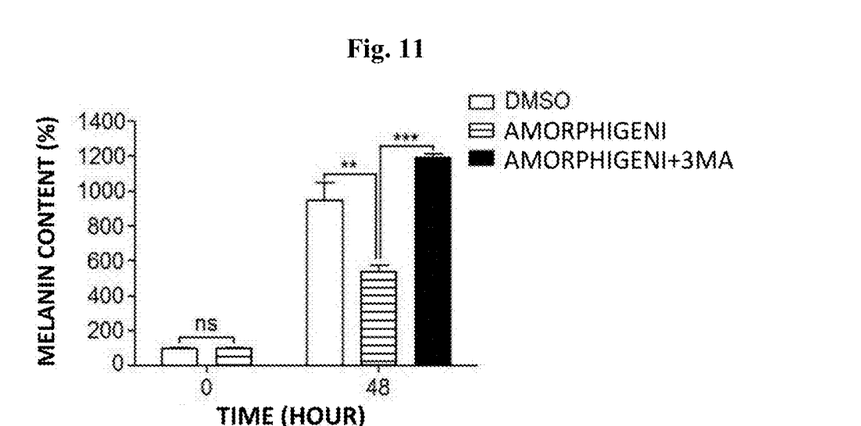
FIG. 11 shows a decrease in the content of previously formed melanin in B16F10 mouse melanoma cells when melanosome synthesis is carried out by a treatment with α-MSH followed by a treatment with amorphigeni and 3-MA (3-methyladenine) according to one example of the present invention.
Figure 12:
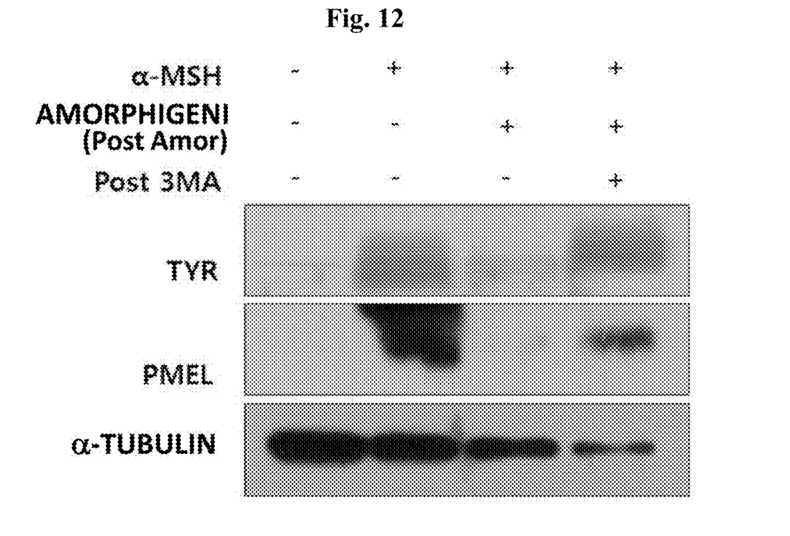
FIG. 12 shows a change in the expression level of tyrosinase and PMEL in B16F10 mouse melanoma cells when melanosome synthesis is carried out by a treatment with α-MSH followed by a treatment with amorphigeni and 3-MA (3-methyladenine) according to one example of the present invention. α-Tubulin is a loading control; and 3-MA is an autophagy inhibitor.

Furthermore, in order to see whether or not amorphigeni causes degradation of previously produced melanosomes via autophagy, B16F10 melanin cells were treated with α-MSH for 48 hours to have synthesis of melanosome. After that, the cells were treated with 3MA as an autophagy inhibitor for 48 hours. Then, the melanin content and protein expression level of tyrosinase and PMEL were measured (ns=no significance, *$P \leq 0.05$, $P \leq 0.01$, *$P \leq 0.001$). As a result, as shown in FIG. 11 and FIG. 12, the cells treated with α-MSH, amorphigeni, and 3MA all together can have the melanin content that has increased again compared to the content lowered by a treatment with α-MSH and amorphigeni, and the protein expression amount of tyrosinase and PMEL has also increased in the cells treated with α-MSH, amorphigeni, and 3MA all together.

Accordingly, it is believed that the autophagy induced by amorphigeni of the present invention can regulate the depigmentation in melanocyte, and the melanosome autophagy-specific inducing agent like amorphigeni can be utilized as a very useful material for developing a skin whitening preparation and a skin lightening preparation.

---

The invention claimed is:

1. A method of whitening the skin of a subject, the method comprising:

preparing a composition comprising amorphigeni represented by Chemical Formula 1 or a salt thereof as an effective ingredient:

Chemical Formula 1 and applying the composition to the skin of the subject, wherein the amorphigeni is prepared by a process comprising:

obtaining an extract from roots of *Amorpha fruticosa*;

concentrating the extract;

eluting the extract to obtain fractions; and obtaining a fraction containing the amorphigeni in the largest amount.

2. The method of claim 1, wherein the composition is a cosmetic composition which is a formulation selected from the group consisting of a solution, a suspension, an emulsion, a paste, a gel, a créme, a lotion, a powder, a soap, a surfactant-containing cleanser, an oil, a powder foundation, a foundation, a wax foundation and a spray.

3. The method of claim 1, wherein the composition comprises the salt, and the salt is an acid addition salt formed with a free acid.

4. The method of claim 2, wherein the formulation is the paste, the creme, or the gel; and the formulation composition comprises an animal fiber, a plant fiber, wax, paraffin, starch, tragacanth, a cellulose derivative, polyethylene glycol, silicone, bentonite, silica, talc, zinc oxide, or a combination thereof as a carrier component.

5. The method of claim 2, wherein the formulation is the powder or the spray; and the formulation comprises lactose, talc, silica, aluminum hydroxide, calcium silicate, polyamide powder or a combination thereof as a carrier component.

6. The method of claim 2, wherein the formulation is the spray; and the formulation further comprises chlorofluorohydrocarbon, propane-butane, or dimethyl ether.

7. The method of claim 2, wherein the formulation is the solution or the emulsion; and the formulation comprises a solvent, a solubilizing agent, or an emulsifying agent as a carrier component.

8. The method of claim 2, wherein the formulation is the suspension; and the formulation comprises a liquid phase diluent, a suspending agent, microcrystalline cellulose, aluminum metahydroxide, bentonite, agar, or tragacanth as a carrier component.

9. The method of claim 2, wherein the formulation is the surfactant-containing cleanser; and the formulation comprises aliphatic alcohol sulfate, aliphatic alcohol ether sulfate, sulfonsuccinic acid monoester, acethionate, an imidazoilum derivative, methyl taurate, sarcosinate, fatty acid amide ether sulfate, alkylamidobetain, aliphatic alcohol, fatty acid glyceride, fatty acid diethanolamide, plant oil, a linolin derivative, or ethoxylated glycerol fatty acid ester.

10. The method of claim 2, wherein the formulation further comprises an additional skin whitening active component selected from the group consisting of kojic acid, albutin, ascorbic acid, hydroquinone, resorcinol, cycloalkanone, methylene dioxyphenylalkanol, 2,7-dinitroindazole, a bearberry extract, a rice extract, a liquorice extract, and a derivative thereof.

11. The method of claim 1, wherein the composition further comprises a vehicle including a fluorescent material, a bactericidal agent, a hydrotrope, a moisturizing agent, an aroma, an aromatic carrier, a protein, a solubilizing agent, a sugar derivative, a sunshine blocking agent, a vitamin, a plant extract, or a combination thereof.

12. The method of claim 1, wherein the composition is a pharmaceutical composition that is a formulation selected from the group consisting of an injection solution, a créme, a patch, a spray, an ointment, a hard solid, a lotion, a liniment, a paste, and a cataplasma.

13. The method of claim 12, wherein the pharmaceutical composition further comprises a pharmaceutically acceptable carrier selected from the group consisting of lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oil, and a combination thereof.

14. The method of claim 12, wherein the pharmaceutical composition further comprises a lubricating agent, a humidifying agent, a sweetening agent, a flavoring agent, an emulsifying agent, a suspending agent, a preservative, or a combination thereof.

15. The method of claim 1, wherein the subject has a melanin hyperpigmentation disorder.

16. The method of claim 15, wherein the melanin hyperpigmentation disorder is freckles, senile spots, chloasma, small brown spots, brown or black moles, sunshine pigment spots, cyanic melisma, hyperpigmentation after drug use, gravidic chloasma, or hyperpigmentation after inflammation caused by lesions or skin inflammation.

17. The method of claim 15, wherein the composition is prepared as any one formulation selected from an injection solution, créme, a patch, a spray, an ointment, a hard solid, a lotion, a liniment, a paste, and a cataplasma.

18. The method of claim 15, wherein the composition is a pharmaceutical composition comprising a pharmaceutical carrier.

19. A method of whitening the skin of a subject, the method comprising:
  preparing an isolated amorphigeni represented by Chemical Formula 1 or a salt thereof:

Chemical Formula 1 preparing a composition comprising the isolated amorphigeni; and
  applying the composition to the skin of the subject.

20. The method of claim 19, wherein the isolated amorphigenin has a purity of at least 70%.

* * * * *